US010188679B2

(12) United States Patent
Eisenbach-Schwartz et al.

(10) Patent No.: US 10,188,679 B2
(45) Date of Patent: Jan. 29, 2019

(54) HUMAN MONOCYTE SUB-POPULATION FOR TREATMENT OF EYE DISEASES AND DISORDERS

(71) Applicant: Yeda Research and Development Co. Ltd, Rehovot (IL)

(72) Inventors: Michal Eisenbach-Schwartz, Rehovot (IL); Ester Yoles, Nahal Soreq (IL); Inbal Benhar Bar-On, Rehovot (IL)

(73) Assignee: Yeda Research and Development Co. Ltd, Rehovot (IL)

( * ) Notice: Subject to any disclaimer, the term of this patent is extended or adjusted under 35 U.S.C. 154(b) by 332 days.

(21) Appl. No.: 14/898,732

(22) PCT Filed: May 22, 2014

(86) PCT No.: PCT/IL2014/050463
§ 371 (c)(1),
(2) Date: Dec. 15, 2015

(87) PCT Pub. No.: WO2014/188436
PCT Pub. Date: Nov. 27, 2014

(65) Prior Publication Data
US 2016/0166612 A1  Jun. 16, 2016

Related U.S. Application Data

(60) Provisional application No. 61/915,069, filed on Dec. 12, 2013, provisional application No. 61/826,159, filed on May 22, 2013.

(51) Int. Cl.
| A61K 35/17 | (2015.01) |
| C12N 5/078 | (2010.01) |
| A61K 35/15 | (2015.01) |
| A61K 39/00 | (2006.01) |
| C12N 5/0786 | (2010.01) |
| A61K 9/00 | (2006.01) |
| A61K 35/12 | (2015.01) |

(52) U.S. Cl.
CPC ............ *A61K 35/15* (2013.01); *A61K 9/0048* (2013.01); *A61K 35/17* (2013.01); *A61K 39/0008* (2013.01); *C12N 5/0645* (2013.01); *A61K 2035/122* (2013.01); *A61K 2039/5154* (2013.01)

(58) Field of Classification Search
None
See application file for complete search history.

(56) References Cited

FOREIGN PATENT DOCUMENTS

| WO | 03/044037 A2 | 5/2003 | |
| WO | 2010/096177 A1 | 8/2010 | |
| WO | 2013/088441 A1 | 6/2013 | |
| WO | WO 2013088441 A1 * | 6/2013 | ............ A61K 35/14 |

OTHER PUBLICATIONS

Onishi, "A large quantity of CD3-/CD19-/CD16-lymphocytes in malignant pleural effusion from a patient with recurrent cholangio cell carcinoma" Immunologic Investigations, May 2002, 31(2), 121-135. (Year: 2002).*
International Preliminary Report on Patentability and Written Opinion, PCT/IL2014/050463, dated Nov. 24, 2015.
Donnelly et al. Deficient CX3CR1 Signaling Promotes Recovery after Mouse Spinal Cord Injury by Limiting the Recruitment and Activation of Ly6Clo/iNOS+ Macrophages, The Journal of Neuroscience, Jul. 6, 2011, 31(27):9910-9922.
Ingersoll et al., Comparison of gene expression profiles between human and mouse monocyte subsets, Blood Journal, Jan. 21, 2010, 115 (3).
Knoller et al., Clinical experience using incubated autologous macrophages as a treatment for complete spinal cord injury: Phase I study results, J Neurosurg Spine 3:173-181, 2005.
London et al., Neuroprotection and progenitor cell renewal in the injured adult murine retina requires healing monocyte-derived macrophages, The Journal of Experimental Medicine, Published Jan. 10, 2011.
Shechter et al., Infiltrating Blood-Derived Macrophages Are Vital Cells Playing an Anti-inflammatory Role in Recovery from Spinal Cord Injury in Mice, PLOS Medicine Jul. 2009, vol. 6, Issue 7, e1000113.
Gaudana, et al., Ocular Drug Delivery, AAPS J. 12(3): 348-360 (2010).

* cited by examiner

*Primary Examiner* — Robert J Yamasaki
*Assistant Examiner* — Charles Zoltan Constantine
(74) *Attorney, Agent, or Firm* — UltimatEdge IP Law Group, P.C.; Dean G. Stathakis

(57) ABSTRACT

A monocyte subpopulation having a low relative amount, or substantially devoid, of $CD3^+$ cells, $CD19^+$ cells, $CD56^+$ cells and optionally $CD16^+$ cells is provided, wherein the monocyte subpopulation is for use in inhibition of neuronal degeneration, protection of neurons from glutamate toxicity or promotion of nerve regeneration in the retina or optic nerve, wherein the retina or optic nerve is damaged by a disease, disorder or condition of the eye, or for treatment of an inflammatory disease, disorder or condition of the eye.

20 Claims, 5 Drawing Sheets

HUMAN MONOCYTE SUB-POPULATION FOR TREATMENT OF EYE DISEASES AND DISORDERS

CROSS-REFERENCES TO RELATED APPLICATIONS

The 35 U.S.C. § 371 application is a US national stage entry of International Application PCT/IL2014/050463, filed May 22, 2014, and claims the benefit of priority and is entitled to the filing date of U.S. Provisional Patent Application 61/915,069, filed on Dec. 12, 2013 and U.S. Provisional Patent Application 61/826,159, filed on May 22, 2013, the contents of each of which are hereby incorporated by reference in its entirety.

FIELD OF THE INVENTION

The present invention relates in general to sub-populations of human monocytes useful in the treatment of retinal and optic nerve degeneration with or without inflammatory components and in the treatment of inflammatory diseases, disorders or conditions of the eye.

BACKGROUND OF THE INVENTION

Neuronal death after initial insult to central nervous system (CNS) tissue leads to a vicious cycle of neurotoxicity that, unless homeostasis is rapidly restored, results in spread of damage (Doble, 1999). In case that the evoked mechanisms of protection and repair are insufficient, further death of neurons will occur, a phenomenon relevant to many CNS pathologies regardless of their etiology or primary cause of damage including the nerve cells of the retina and the optic nerve, which are part of the CNS. In all deviation from homeostasis resident immune cells are activated. In the CNS such immune cells are the resident microglia. If these cells are not sufficiently activated, or activated but are not resolved on time, they may enter into a vicious cycle of local inflammation, which is not the primary cause of the pathology but may be part of its progression. Halting insufficient local immune activity of an immune activity that is not arrested on time requires the help of inflammation-resolving cells, circulating monocytes that are freshly recruited and can be locally educated to become inflammation-resolving cells. Below we will summarize eye diseases in which immune cells have been implicated.

Age-related macular degeneration. (AMD) is a disease affecting the macular region of the eye, which is the area in the retina where the sharp vision is obtained, manifested by atrophy of the retinal pigment epithelial layer below the retina and loss of photoreceptors (rods and cones). About 10% of AMD patients suffer from neovascular or exudative macular degeneration caused by the deterioration of the central portion of the retina due to abnormal blood vessel growth. Diverse cellular processes have been implicated in AMD pathogenesis, including inflammation, oxidative stress, altered cholesterol metabolism and/or impaired function of the retinal pigment epithelium. The proliferation of abnormal blood vessels in the retina is stimulated by vascular endothelial growth factor (VEGF).

Uveitis is thought to be caused by autoimmune disorders such as rheumatoid arthritis or ankylosing spondylitis, infection, or exposure to toxins. However, in many cases the cause is unknown. The most common form of uveitis is anterior uveitis, which involves inflammation in the front part of the eye. The inflammation may be associated with autoimmune diseases, but most cases occur in healthy people. Posterior uveitis is a potentially blinding ocular inflammatory condition that affects the choroid of the eye and the neural retina. Many studies have identified macrophages as key players in experimental autoimmune uveitis (EAU), a model for human posterior uveitis, mainly in the context of the induction and effector phase of the disease, although several reports have indicated the presence of macrophages in the resolution stage, as well. However, in most of these studies there was no functional discrimination between resident microglia and infiltrating macrophages. In addition, the characterization of distinct subsets of monocyte-derived macrophages and their functions at different phases of the disease in vivo have not yet been reported.

Retinitis pigmentosa (RP), a form of retinal dystrophy, is a group of inherited disorders characterized by progressive peripheral vision loss and night vision difficulties (nyctalopia) that can lead to central vision loss. RP is caused by abnormalities of the photoreceptors (rods and cones) or the retinal pigment epithelium (RPE) of the retina leading to progressive sight loss. Clinical evidence of sustained chronic inflammatory reaction in RP was shown, suggesting that inflammation may underlie the pathogenesis of RP (Yoshida et al., 2013).

Diabetic retinopathy, is retinopathy caused by complications of diabetes, which can eventually lead to blindness. Diabetes causes a number of metabolic and physiologic abnormalities in the retina, but which of these abnormalities contribute to recognized features of diabetic retinopathy (DR) is less clear. Many of the molecular and physiologic abnormalities that have been found to develop in the retina in diabetes are consistent with inflammation. Moreover, a number of anti-inflammatory therapies have been found to significantly inhibit development of different aspects of DR in animal models (Tang et al., 2011).

Glaucoma is a slow-progressing optic neuropathy with a high incidence in the elderly population (approximately 1%). Until recently, it was associated with high intraocular pressure (TOP) and therefore attempts have been focused on slowing down the disease progression by anti-hypertensive drugs. Over the years, it became apparent that glaucoma is a family of diseases and not all are associated with pressure. Moreover, it became clear that even when the disease is associated with pressure, the latter may be reduced to normal and even below normal values and degeneration may continue. An ongoing discussion among clinicians has questioned whether the continuous degeneration in glaucomatous patients, in spite of normal IOP values, is a reflection of the existence of additional risk factors besides pressure or a reflection of the increased vulnerability of the remaining neurons and fibers and thus the need to reduce IOP below normal values. Glaucoma results in neurodegeneration especially of the retinal ganglion cells (RGCs) leading to progressive loss of visual field up to loss of vision.

Etiology. Acute and/or chronic neuronal loss in the adult CNS results in the irreversible loss of function due to the very poor ability of mature nerve cells to proliferate and compensate for the lost neurons. Thus attenuating or reducing neuronal loss is essential for preservation of function. In most of the neurodegenerative diseases the etiology is not clear, hence they are incurable. Nevertheless, there are some primary and secondary risk factors, which are the target for therapeutic intervention aiming at inhibiting or attenuating progress of neuronal loss, collectively termed as neuroprotective therapy. Some of the risk factors are disease-specific but others, like excitatory amino acids, free radicals and nitric oxide, are common to all the neurodegenerative disorders. These factors are essential self-components in the healthy CNS, but with their accumulation in excess amounts in the degenerative tissue, they become cytotoxic leading to the spread of damage beyond the initial cause of neuron death.

Glutamate is one of the most common mediators of toxicity in acute and chronic degenerative disorders (Pitt et al., 2000). Glutamate is a primary excitatory neurotransmitter in the human CNS. L-glutamate is present at a majority of synapses and is capable of displaying dual activity: it plays a pivotal role in normal functioning as an essential neurotransmitter, but becomes toxic when its physiological levels are exceeded.

Current disease management. There is currently no cure for neurodegenerative diseases, and treatment focuses on alleviating or managing symptoms. The neuroprotective therapy has failed to show efficacy in the vast majority of the clinical studies that were conducted so far. Regarding AMD, anti-angiogenics or anti-VEGF agents can cause regression of the abnormal blood vessels and improve vision when injected directly into the vitreous humor of the eye Regenerative medicine and protective autoimmunity Regenerative medicine is an emerging field that aims to repair, replace, and/or regenerate damaged tissues and organs by stimulating previously irreparable organs into healing themselves including tissue engineering, biomaterials, and cellular therapy. Cell renewal, a common healing process in peripheral tissues, is limited in the adult neural retina as it is in the rest of the CNS. However, a quiescent population of retinal progenitor cells (RPCs) continues to exist in the retinal ciliary body (CB) throughout adulthood and has the potential to differentiate into various cells of the retina or to possibly serve as a source of immunomodulatory or neurotropic agents. This dormant progenitor cell niche was reported to be stimulated after retinal injury, although the underlying mechanisms are yet to be revealed. Unraveling the healing processes that operate in response to injury and finding ways to enhance them could lead to the development of new therapies for promoting neuroprotection and cell renewal, which is among the research goals in this field.

Outside the CNS, healing processes require the help of the immune system for clearance of dead cells and cell debris and for support of regrowth and cell renewal. These processes are mediated, in part, by different subsets of macrophages that acquire discrete phenotypes over the time course of healing. In the course of a response to any insult, there is a pivotal stage of termination of the local immune response involving monocyte-derived macrophages, which contribute to an overall anti-inflammatory milieu and produce growth factors needed for regeneration.

Infiltration/recruitment of peripheral blood into the lesion site is controlled by signals elicited from the lesion site, which affects the brain-cerebrospinal fluid (CSF) barrier. The limited spontaneous recovery following CNS injury can be attributed in part to the inadequate, untimely, spontaneous recruitment of the effective subset of monocytes to the lesion site. The above considerations have led the inventors to follow a novel physiological approach that employs the body's professional healing system, the immune system, to contend with the consequences of CNS damage leading to neuroprotection and restoration.

It has been shown in the laboratory of the inventors that blood-derived monocytes incubated with skin segments acquired a non-inflammatory phenotype similar to anti-inflammatory M2 monocytes described in the literature. Injection of the monocytes into the injured spinal cord induced better recovery from spinal cord injury (SCI) in rats (U.S. Pat. Nos. 5,800,812; 6,117,424; and 6,267,955). This approach was tested in a clinical study on patients suffering from acute sever spinal cord injury showing encouraging results (WO 03/044037; Knoller et al., 2005). The inventors have also shown that enrichment of peripheral blood monocytic pool with bone-marrow derived $CD115^+$ cells augmented functional recovery following SCI in mice (Shechter et al., 2009).

Blood monocytes are heterogenic cellular population with different characteristics and activities. Utilizing blood monocytes for therapeutic purposes requires the identification of the cells with harmful functions and those that are beneficial.

In humans, it was proposed that the expression of CD16 on monocytes can distinguish between three subsets, namely $CD14^{++}CD16^-$ (classical) $CD14^{++}CD16^{++}$ (intermediate) and $CD14^{dim}CD16^{++}$ (non-classical) monocytes, but their role in physiological and pathological conditions is not fully understood. Recently, the inventors discovered that $CD16^+$ enriched monocytes, upon injection into the CSF of animals following spinal cord injury, attenuates spontaneous recovery as compared with animals that received total monocytic sub-population. It was also found that a monocytic sub-population devoid of CD16 expressing cells ($CD16^-$), are beneficial for recovery following spinal cord injury (PCT/IL2012/050522).

SUMMARY OF INVENTION

This disclosure generally relates, in part, to a monocyte subpopulation of peripheral blood mononuclear cells (PBMCs) having a low relative amount, or substantially devoid, of $CD3^+$ cells, $CD19^+$ cells and $CD56^+$ cells, or a monocyte subpopulation of PBMCs having a low relative amount, or substantially devoid, of $CD3^+$ cells, $CD19^+$ cells, $CD56^+$ cells and $CD16^+$, for use in inhibition of neuronal degeneration, protection of neurons from glutamate toxicity or promotion of nerve regeneration in the retina or optic nerve, wherein the retina or optic nerve is damaged by a disease, disorder or condition of the eye.

Also provided herein is a monocyte subpopulation of PBMCs having a low relative amount, or substantially devoid, of $CD3^+$ cells, $CD19^+$ cells and $CD56^+$ cells, or a monocyte subpopulation of PBMCs having a low relative amount, or substantially devoid, of $CD3^+$ cells, $CD19^+$ cells, $CD56^+$ cells and $CD16^+$, for use in treatment of an inflammatory disease, disorder or condition of the eye.

Further provided herein are compositions comprising a monocyte subpopulation of PBMCs having a low relative amount, or substantially devoid, of $CD3^+$ cells, $CD19^+$ cells and $CD56^+$ cells, or a monocyte subpopulation of PBMCs having a low relative amount, or substantially devoid, of $CD3^+$ cells, $CD19^+$ cells, $CD56^+$ cells and $CD16^+$, for inhibition of neuronal degeneration, protection of neurons from glutamate toxicity or promotion of nerve regeneration in the retina or optic nerve, wherein the retina or optic nerve is damaged by a disease, disorder or condition of the eye.

The disclosure also generally relates to compositions comprising a monocyte subpopulation of PBMCs having a low relative amount, or substantially devoid, of $CD3^+$ cells, $CD19^+$ cells and $CD56^+$ cells, or a monocyte subpopulation of PBMCs having a low relative amount, or substantially devoid, of $CD3^+$ cells, $CD19^+$ cells, $CD56^+$ cells and $CD16^+$, for use in treatment of an inflammatory disease, disorder or condition of the eye.

Further provided herein are methods for inhibition of neuronal degeneration, protection of neurons from glutamate toxicity or promotion of nerve regeneration in the retina or optic, wherein the retina or optic nerve is damaged by a disease, disorder or condition of the eye said method comprising administering to an individual in need an effective amount of a monocyte subpopulation of PBMCs having a low relative amount, or substantially devoid, of $CD3^+$ cells, $CD19^+$ cells and $CD56^+$ cells, or a monocyte subpopulation of PBMCs having a low relative amount, or substantially devoid of $CD3^+$ cells, $CD19^+$ cells, $CD56^+$ cells and $CD16^+$ cells.

The disclosure also generally relates to methods for treatment of an inflammatory disease, disorder or condition of the eye, comprising administering to an individual in need an effective amount of a monocyte subpopulation of PBMCs having a low relative amount, or substantially devoid of, $CD3^+$ cells, $CD19^+$ cells and $CD56^+$ cells, or a monocyte subpopulation of PBMCs having a low relative amount, or substantially devoid, of $CD3^+$ cells, $CD19^+$ cells, $CD56^+$ cells and $CD16^+$ cells.

DETAILED DESCRIPTION OF THE INVENTION

Figure 1A:
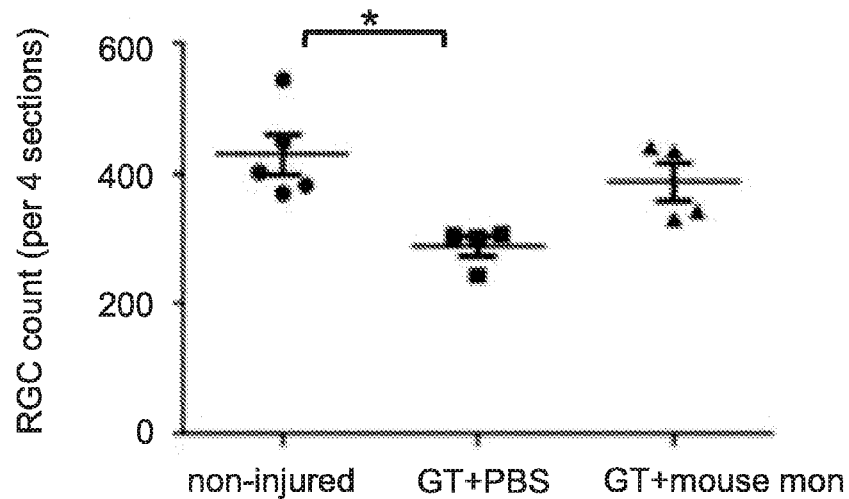
FIGS. 1A-E show that syngeneic monocyte injection to the vitreous is neuroprotective after glutamate intoxication. Retinal Ganglion Cells (RGCs) were quantified in sections of noninjured, injured and monocyte-treated retinas 7 days after glutamate intoxication. Quantification of $Brn3a^+$ RGCs in 4 sections per case, presented as count (A) or as percent survival relative to noninjured retina (B). (C-E) Representative micrographs of RGCs in retinas of noninjured (C) and injured mice (D-E) that were intravitreally injected with either PBS (D) or mouse monocytes (E), labeled with the RGC marker, Brn3a (red; scale bar 100 μm). Arrows point to $Brn3a^+$ RGCs. Note the loss of RGCs after the injury, as seen in the PBS treated group, and the sparing of RGCs in the monocyte (mouse mon) treated retina. Bar graphs throughout the figure show mean±SE of each group. *, $P<0.05$; **, $P<0.01$. GT—glutamate; mon—monocytes; RGC—retinal ganglion cell.

The present inventors have previously reported that after glutamate eye intoxication, monocyte-derived macrophages infiltrate the damaged retina of mice. Inhibition of this infiltration results in reduced survival of Retinal Ganglion Cells (RGCs) and diminished numbers of proliferating retinal progenitor cells (RPCs) in the ciliary body. Enhancement of the circulating monocyte pool leads to increased RGC survival and RPC renewal. The infiltrating monocyte-derived macrophages skews the milieu of the injured retina toward an anti-inflammatory and neuroprotective one and down-regulates accumulation of other immune cells, thereby resolving local inflammation and enhancing tissue repair (London et al., 2011, incorporated by reference as if fully disclosed herein). Glutamate, at levels that exceed the physiological one, is one of the early factors that contribute to the process of self-perpetuating degeneration, irrespectively of the primary risk factor.

The present inventors have also recently found that a sub-population of blood derived human monocytes that is defined by the absence, near absence, or low relative number of cells expressing CD3, CD19, CD56 and optionally CD16, is capable of homing from the cerebrospinal fluid (CSF) to the site of injury in the spinal cord, and promote there tissue restoration and improved functional recovery (PCT/IL2012/050522). It has further been recently found by the present inventors that the beneficial effect of the cells in healing the wounded spinal cord is obtained either by cells activated by co-incubation with a piece of skin administered into the spinal cord at the borders of the lesion, or by administering un-activated cells into the CSF of injured spinal cord.

It has now been found in accordance with the present invention, that intravitreal injection of mouse $CD115^+$ bone marrow monocyte cells have a protective effect on mouse retinal ganglion survival after glutamate intoxication (Example 4).

A cell expressing on its surface a certain identifiable marker, such as a Cluster of Differentiation (CD) molecule X is referred to herein as CD $X^+$. For example, a cell expressing on its surface a CD3 molecule is referred to herein as $CD3^+$. The relative amount of the CD molecule expressed on the cell surface is referred to by adding "+", e.g. $CD3^{++}$ for high amounts of CD molecules, or the term "dim", showing a relative low level of CD molecules. A population of cells comprising a cell type defined by the expression of a certain CD, a population relatively enriched with these cells, or a population lacking such cells, is designated $CD^+$, $CD^{++}$ or $CD^-$, respectively.

Thus, in an embodiment, the human monocyte subpopulation of PBMCs has a low relative amount, or is substantially devoid, of $CD3^+$ cells, $CD19^+$ cells and $CD56^+$ cells. For example, the PBMCs of the present invention may have a low relative amount of $CD3^+$ cells and be substantially devoid of $CD19^+$ cells and $CD56^+$ cells.

In one embodiment, also $CD16^+$ cells have been removed from the PBMC sub-population resulting in a monocyte subpopulation of PBMCs further substantially devoid of $CD16^+$ cells, i.e. a monocyte subpopulation having a low relative amount, or substantially devoid, of $CD3^+$ cells, $CD19^+$ cells, $CD56^+$ cells and $CD16^+$ cells. For example, the PBMCs of the present invention may have a low relative amount of $CD3^+$ cells and be substantially devoid of $CD19^+$ cells, $CD56^+$ cells and $CD16^+$ cells.

The typical antigens that are used to differentiate between the various monocyte sub-populations in non-human animals and in humans are different, and thus a certain mouse cell population may be identified using a marker that is different than the marker used to identify the corresponding cell population in humans. For example, mouse $CD115^+$ monocytes, used in Example 4 herein below, is divided into two sub-populations; GR1$^+$ and GR1$^-$, while the corresponding monocyte population in human is divided into three sub-populations defined based on their expression of the membrane markers CD14 and CD16 (Geissman et al. (2008) Blood monocytes: distinct subsets, how they relate to dendritic cells, and their possible roles in the regulation of T-cell responses. Immunology and Cell Biology (2008) 86, 398-408).

The term "peripheral blood mononuclear cell (PBMC)" as used herein refers to any blood cell having a round nucleus, such as a lymphocyte, a monocyte or a macrophage. Methods for isolating PBMCs from blood are readily apparent to those skilled in the art. An non-limiting example is the extraction of these cells from whole blood using ficoll, a hydrophilic polysaccharide that separates layers of blood, with monocytes and lymphocytes forming a buffy coat under a layer of plasma or by leukapheresis, the preparation of leukocyte concentrates with the return of red cells and leukocyte-poor plasma to the donor.

The phrase "a population of cells substantially devoid of . . . [a certain cell]" is used herein interchangeably with the phrase "near absence of" and preferably includes a population of cells lacking a certain cell type, or alternatively comprising a relative amount of a certain cell type not exceeding about 0.05%, 0.1%, 0.5%, 1%, 2%, 3%, 4%, or 5% of the total number of cells in said population of cells. The phrase "a population of cells having a low relative amount of . . . [a certain cell]" refers to a population of cells being present at a low relative amount of cells in comparison with the relative amount of the same kind of cells in a freshly isolated and unprocessed human PBMC population, but at a higher relative amount than the population being "substantially devoid" of this cell population.

Thus, in an embodiment, the relative amount of each one of CD19$^+$ cells and CD56$^+$ cells is not exceeding about 0.05%, 0.1%, 0.5%, 1%, 2%, 3%, 4%, or 5% of the total number of cells in the PBMC population. In certain embodiments, the relative amount of CD16$^+$ cells in the monocyte subpopulation substantially devoid of CD3$^+$ cells, CD19$^+$ cells, CD56$^+$ cells and CD16$^+$ cells is not exceeding about 0.05%, 0.1%, 0.5%, 1%, 2%, 3%, 4%, or 5% of the total number of cells.

A normal human PBMC cell population comprises inter alia more than 70% CD3$^+$ cells and about 10-15% monocytes, so for a "population of cells having a low relative amount of CD3$^+$ cells", the relative amount of CD3$^+$ cells was reduced from more than 70% to about 10%, 15%, 20% or 25% of the total number of cells in the PBMC population. However, it is also conceivable that with improved methods of cell separation the PBMC population of the present invention will have near absence of CD3$^+$ cells, i.e. their relative amount being about 0.05%, 0.1%, 0.5%, 1%, 2%, 3%, 4%, or 5% of the total number of cells in the PBMC population.

In an embodiment, the monocyte subpopulations having a low relative amount, or substantially devoid, of CD3$^+$ cells, CD19$^+$ cells and CD56$^+$ and optionally also substantially devoid of CD16$^+$ cells, are substantially enriched in CD14$^+$ cells.

The phrase "a population of cells substantially enriched in" refers to a population of cells comprising a relative amount of a certain cell type exceeding about 60%, 70%, 80%, 90%, 95% or 99% of the total number of cells in said population of cells.

In an embodiment, the monocyte subpopulation of PBMCs having a low relative amount, or substantially devoid, of CD3$^+$ cells, CD19$^+$ cells and CD56$^+$ cells comprises at least about 60% CD14$^+$ cells, and the monocyte subpopulation substantially devoid of CD3$^+$ cells, CD19$^+$ cells, CD56$^+$ cells and CD16$^+$ cells comprises at least about 80% CD14$^+$ cells. Thus, the monocyte subpopulation as defined herein is also referred to herein as a CD14$^{++}$, CD16$^-$ population.

In some embodiments, the monocyte subpopulation of the present invention is useful for inhibition of neuronal degeneration, protection of neurons from glutamate toxicity or promotion of nerve regeneration in the retina or optic nerve, wherein the retina or optic nerve is damaged by a disease, disorder or condition of the eye.

For example, in one embodiment, the disease, disorder or condition that cause neuronal degeneration in the eye and is exacerbated by glutamate toxicity is selected from a retinal degeneration disorder selected from age-related macular degeneration or retinitis pigmentosa; anterior ischemic optic neuropathy; glaucoma or uveitis. These diseases cause damage to the nerve tissue and in certain embodiments, administration of the monocyte subpopulation of the present invention promote nerve regeneration. The invention also contemplates the treatment of chronic or acute retinopathy, retinopathy as a result of systemic disease such as diabetes or hypertension, radiation retinopathy and solar retinopathy.

Alterations in retinal homeostasis secondary to acute insult, aging, toxins, metabolic abnormalities, altered vascular perfusion, or degenerative genetic conditions may initiate various inflammatory cascades in the eye. In all of these settings, a prolonged, dysregulated immune response may itself be pathologic, contributing to both the pathogenesis of retinal diseases as well as vision threatening complications. Since the blood derived monocytes act to resolve inflammation and restore homeostasis, helping the tissue to heal itself, the present invention is further directed to the treatment of inflammatory diseases of the eye that do not necessary lead to neurodegeneration in the eye. In some embodiments, the monocyte subpopulation used in the present invention will be effective in treating inflammatory diseases of the eye, such as scleritis (inflammation of the sclera); keratitis (inflammation of the cornea); corneal ulcer (loss of the surface epithelial layer of the eye's cornea); snow blindness (a painful condition caused by exposure of unprotected eyes to bright light); Thygeson's superficial punctate keratopathy; corneal neovascularization; Fuchs' dystrophy (cloudy morning vision); keratoconus (change in the thickness and shape of the cornea); keratoconjunctivitis sicca (dry eyes); or iritis (inflammation of the iris). In certain embodiments, the PBMCs are useful for inhibition of neuronal degeneration, protection of neurons from glutamate toxicity or promotion of nerve regeneration in the retina or optic nerve, wherein the retina or optic nerve is damaged by an inflammatory disease, disorder or condition of the eye.

In one embodiment, the monocyte subpopulation of PBMCs used in any one of the aspects of the present invention comprises human PBMCs.

The monocyte subpopulation of human PBMCs may be isolated from autologous PBMCs, i.e. blood is collected from a patient in need of treatment of an eye disease, a PBMC monocyte subpopulation according to the present invention is prepared as defined herein below, and then administered back to the patient.

Alternatively, the monocyte subpopulation of human PBMCs may be isolated from allogeneic PBMCs, i.e. blood is collected from a genetically similar, but not identical, donor, a PBMC monocyte subpopulation according the present invention is prepared as defined herein below and optionally stored in a cell-bank before being administered to the patient.

In one embodiment, the monocyte subpopulation of PBMCs is formulated for injection, for example for injection into the eye.

Also provided herein is a composition comprising a monocyte subpopulation of PBMCs as defined herein above, for inhibition of neuronal degeneration, protection of neurons from glutamate toxicity or promotion of nerve regeneration in the retina or optic nerve, wherein the retina or optic nerve is damaged by a disease, disorder or condition of the eye, or for treatment of an inflammatory disease, disorder or condition of the eye. The composition may comprise cells of the monocyte subpopulation of PBMCs suspended in a pharmaceutically acceptable carrier adapted for injection, for example for administration into the eye.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

The term "carrier" refers to a diluent, adjuvant, excipient, or vehicle with which the cells are administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

The administration of the cells or the composition into the eye may be via intra-vitreal injection or sub-retinal injection.

It has recently been found by the inventors that the PBMC monocyte subpopulation, upon homing to the boundaries of an injury in the spinal cord, mitigates the injury and improves functional recovery, whether the cells have previously been activated by co-culture with a piece of skin, i.e. they are skin-activated cells, or whether they are non-activated (PCT/IL2012/050522).

Thus, for example, the cells of the monocyte subpopulation of PBMCs of the present invention injected into the eye may be skin-activated cells.

Alternatively, the cells of the monocyte subpopulation of PBMCs of the present invention injected into the eye may be non-activated cells.

As disclosed above, the monocyte subpopulation of PBMCs as defined herein and the composition comprising them, are useful for treatment of a neurodegenerative diseases, disorders or conditions of the eye. In particular, the treatment comprises promotion of neural tissue restoration including, for example, preventing or inhibiting neuronal degeneration, promotion of neuronal survival, axonal regeneration and/or sprouting, neurogenesis in a damaged retina or optic nerve tissue, and/or promotion of functional recovery. It has been shown herein that at least partially, the beneficial effect on the nerve cells results from the modulation of the inflammatory response by the specific monocyte subpopulation of PBMCs as defined herein.

Accordingly, the present invention further provides a method for inhibition of neuronal degeneration, protection of neurons from glutamate toxicity or promotion of nerve regeneration in the retina or optic nerve, wherein the retina or optic nerve is damaged by a disease, disorder or condition of the eye, or for treatment of an inflammatory disease, disorder or condition of the eye, said method comprising administering to an individual in need an effective amount of a monocyte subpopulation of PBMCs as defined herein.

PCT/IL2012/050522 of the same applicant provides a method for isolation from blood of the monocyte subpopulation of human PMBC substantially devoid of $CD3^+$ cells, $CD19^+$ cells and $CD56^+$ cells described herein, comprising the steps: (i) isolating mononuclear cells from blood; and (ii) removing the $CD3^+$ cells, $CD19^+$ cells and $CD56^+$ cells from the mononuclear cells of (i) by contacting said mononuclear cells with anti-$CD3^+$ antibodies, anti-$CD19^+$ antibodies and anti-$CD56^+$ antibodies, each one of which is linked to micro beads, thereby binding said cells to said micro beads, and removing the micro beads, thereby obtaining a monocyte subpopulation of human peripheral blood mononuclear cells (PMBC) from blood having a low relative amount of $CD3^+$ cells and substantially devoid of $CD19^+$ cells and $CD56^+$ cells.

PCT/IL2012/050522 further provides a method for isolation from blood of the PMBC monocyte subpopulation substantially devoid of $CD3^+$ cells, $CD19^+$ cells, $CD56^+$ cells and $CD16^+$ cells, comprising the steps: (iii) isolating mononuclear cells from blood; and (iv) removing the $CD3^+$ cells, $CD19^+$ cells, $CD56^+$ cells and $CD16^+$ cells from the mononuclear cells of (iii) by contacting said mononuclear cells with anti-$CD3^+$ antibodies, anti-$CD19^+$ antibodies, anti-$CD56^+$ antibodies and anti-$CD16^+$ antibodies, each one of which is linked to microbeads, thereby binding said cells to said microbeads, and removing the microbeads, thereby obtaining a monocyte subpopulation of human PMBC from blood having a low amount of $CD3^+$ cells and substantially devoid of $CD19^+$ cells, $CD56^+$ cells and $CD16^+$.

In an embodiment, step (iv), i.e. the removal of $CD3^+$ cells, $CD19^+$ cells, $CD56^+$ cells and $CD16^+$, comprises the sub-steps: (v) removing the $CD3^+$ cells, $CD19^+$ cells and $CD56^+$ cells from the mononuclear cells of (iii) thereby obtaining a monocyte subpopulation of human PMBCs from blood substantially devoid of $CD3^+$ cells $CD19^+$ cells and $CD56^+$ cells; and (vi) removing the $CD16^+$ cells from the PMBC population of (v), thereby obtaining a monocyte subpopulation of human PMBC from blood substantially devoid of $CD3^+$ cells $CD19^+$ cells, $CD56^+$ cells and $CD16^+$ cells.

In one embodiment, the step (iv) is performed in a single step.

The antibodies that capture the cells expressing the desired antigen on their surface, such as CD3, CD19, CD56 and/or CD16, may be biotinylated and then linked to microbeads comprising avidin or streptavidin or equivalent biotin-binding proteins, or the antibodies may be supplied to the cells when already bound to micro beads. The micro beads may be magnetic or non-magnetic and the cells, when bound to the micro beads, may be removed from the solution in which the cells are suspended, by centrifugation, if the micro beads are not magnetic, or by exposure to the magnetic field of a magnet, if they are.

In one embodiment, the antibodies are linked to magnetic micro beads when brought in contact with the cells and the cells are removed by removing the micro beads to which the cells are bound by pulling them from the solution with a magnet.

The above disclosed method may be used for isolating the monocyte subpopulations of human peripheral blood mononuclear cells (PMBC) from blood having a low relative amount, or substantially devoid, of $CD3^+$ cells, $CD19^+$ cells, $CD56^+$ cells and/or $CD16^+$ cells, which are used herein for inhibition of neuronal degeneration, protection of neurons from glutamate toxicity or promotion of nerve regeneration in the retina or optic nerve damaged by a disease, disorder or condition of the eye or for treatment of an inflammatory disease, disorder or condition of the eye.

The invention will now be illustrated by the following non-limiting examples.

EXAMPLES

Material and Methods

Animals. Adult male (8-10 wk old) C57BL/6J mice and heterozygous mutant Cx3cr1GFP/+ mice (B6.129P-Cx3cr1tm1Litt/J, in which one of the CX3CR1 chemokine receptor alleles is replaced with a gene encoding GFP; Jung, S., J. Aliberti, P. Graemmel, M. J. Sunshine, G. W. Kreutzberg, A. Sher, and D. R. Littman. 2000. Analysis of fractalkine receptor CX(3)CR1 function by targeted deletion and green fluorescent protein reporter gene insertion. Mol. Cell. Biol. 20:4106-4114) are used. Additionally, C57BL/6J, heterozygous mutant Cx3cr1GFP/+ mice, MHC-II null mice (B6.129S-H2d1Ab1-Eaa), and IL-10 null mice (B6.129P2-I110tm1Cgn/J; Kühn, R., J. Löhler, D. Rennick, K. Rajewsky, and W. Müller. 1993. Interleukin-10-deficient mice develop chronic enterocolitis. Cell. 75:263-274) are used as donors of monocytes and BM. For CD11c detection, CD11cGFP/+ transgenic mice (B6.FVB-Tg Itgax-DTR/GFP 57Lan/J; Jung, S., D. Unutmaz, P. Wong, G. Sano, K. De los Santos, T. Sparwasser, S. Wu, S. Vuthoori, K. Ko, F. Zavala, et al. 2002. In vivo depletion of CD11c+ dendritic cells abrogates priming of CD8+ T cells by exogenous cell-associated antigens. Immunity. 17:211-220) carrying a transgene encoding a GFP reporter under control of the murine CD11c promoter are used. FoxP3GFP mice were a generous gift from Dr. Alexander Rudensky, Memorial Sloan-Kettering Cancer Center. Transgenic R6/2 mice overexpressing the human gene encoding huntingtin were obtained from the Jackson Laboratory.

If not stated otherwise, animals are supplied by the Animal Breeding Center of The Weizmann Institute of Science. All experiments detailed herein conform to the regulations formulated by the Institutional Animal Care and Use Committee of the Weizmann Institute of Science.

BM Chimeras. [$Cx3cr1^{GFP/+}$>WT] BM chimeras are prepared by subjecting WT recipient mice to lethal whole-body irradiation (950 rad) while shielding the head, as previously described (Rolls, A., R. Shechter, A. London, Y. Segev, J. Jacob-Hirsch, N. Amariglio, G. Rechavi, and M. Schwartz. 2008. Two faces of chondroitin sulfate proteoglycan in spinal cord repair: a role in microglia/macrophage activation. PLoS Med. 5:e171.; Shechter et al., 2009). This shielding prevents a direct insult to the retina and any infiltration of myeloid cells other than that induced by glutamate intoxication. On the subsequent day, mice are reconstituted with $5\times10^6$ BM cells according to a previously described protocol (Shechter et al., 2009). Chimeric mice are subjected to glutamate intoxication or EAU induction protocol 8-12 wk after BM transplantation.

MC-21 Administration. MC-21 (an antibody to CCR2; Mack, M., J. Cihak, C. Simonis, B. Luckow, A. E. Proudfoot, J. Plachý, H. Brühl, M. Frink, H. J. Anders, V. Viehauer, et al. 2001. Expression and characterization of the chemokine receptors CCR2 and CCR5 in mice. J. Immunol. 166:4697-4704) is injected intraperitoneally starting immediately after the injury and throughout the experimental period. In the case of EAU induction, it was injected before or after the peak of EAU, every other day for a total of 5 injections (8 µg per injection).

Adoptive Monocyte Transfer. CD115+ monocytes are isolated as previously reported (Varol, C., L. Landsman, D. K. Fogg, L. Greenshtein, B. Gildor, R. Margalit, V. Kalchenko, F. Geissmann, and S. Jung. 2007. Monocytes give rise to mucosal, but not splenic, conventional dendritic cells. J. Exp. Med. 204:171-180). In brief, BM cells are harvested from the femora and tibiae of mice and enriched for mononuclear cells on a Ficoll density gradient. The CD115+BM monocyte population is isolated through MACS enrichment using biotinylated anti-CD115 antibodies and streptavidin-coupled magnetic beads (MiltenyiBiotec), according to the manufacturer's protocols. After this procedure, monocytes (WT, $Cx_3cr1^{GFP/+}$, IL-10 deficient, or MHC-II deficient) are injected i.v. ($4-5\times10^6$ cells per mouse) on day 1 after injury.

BrdU Regimen. BrdU (Sigma-Aldrich) is dissolved in PBS and injected intravitreally (1 µg/eye), immediately after the insult and for 3 consecutive days, according to a protocol adapted from Zhao et al., 2005 (Growth factor responsive progenitors in the postnatal mammalian retina. Dev. Dyn. 232:349-358). Injections are conducted repeatedly through the same hole without additional tissue penetration. Retinas are expected to exhibit morphology comparable to those that had received single injection. Animals are killed 1 d after the last injection to determine the number of proliferating progenitors or 1 wk after the last injection to detect differentiation. Control animals are administered BrdU intravitreally, using the same regimen, in the absence of glutamate intoxication or elevated IOP. Notably, although we cannot rule out a synergistic effect of the injury followed by repeated BrdU injections on the number of proliferating RPCs, because an identical protocol is applied when comparing retinas/ciliary bodies of animals subjected to the different monocyte manipulations, changes in the numbers of proliferating progenitor cells after these manipulations can most likely be attributed to monocyte-mediated effects.

Fluoro-Gold Labeling of RGCs. For detection of anatomically intact neurons, mice are injected with 1 µl 5% Fluoro-Gold (Fluorochrome) solution in saline on day 3 after injury to both superior colliculi at the following coordinates: 2.92 mm posterior to the bregma, 0.5 mm lateral to the midline, and at a depth of 2 mm from the skull. After 72 h, the mice are killed, their eyes are enucleated, and each retina is flattened as whole mount in 4% paraformaldehyde (PFA) in PBS. The selected fields were located at approximately the same distance from the optic disk (0.3 mm) to overcome the variation in RGC density as a function of distance from the optic disk. Fields were counted under the fluorescence microscope (magnification ×800) by observers blinded to the treatment received by the mouse. The average number of RGCs per field in each retina was calculated. For more details, see Schori et al., 2001 (Vaccination for protection of retinal ganglion cells against death from glutamate cytotoxicity and ocular hypertension: implications for glaucoma. Proc. Natl. Acad. Sci. USA. 98:3398-3403) and Schwartz and Kipnis, 2007 (Model of acute injury to study neuroprotection. Methods Mol. Biol. 399:41-53).

Immunohistochemistry. After perfusion with PBS, eyes were removed, postfixed in 2.5% PFA for 24 h, transferred to 70% ethanol, and then embedded into paraffin, as previously described (Shechter, R., Y. Ziv, and M. Schwartz. 2007. New GABAergic interneurons supported by myelin-specific T cells are formed in intact adult spinal cord. Stem Cells 25:2277-2282). Representative sections were stained with hematoxylin and eosin for histopathological examination. The following antibodies were used for immunolabeling: rabbit anti-GFP (1:100; MBL), mouse anti-Brn3a (1:50; Santa Cruz Biotechnology, Inc.). The M.O.M. immunodetection kit (Vector Laboratories) was used to localize mouse primary monoclonal antibodies. For activated myeloid cell labeling, FITC-conjugated Bandeiraea simplicifolia isolectin B4 (IB-4; 1:50; Sigma-Aldrich) was added for 1 h to the secondary antibody solution. Secondary antibodies used included Cy2/Cy3-conjugated donkey anti-mouse or -rabbit antibodies (1:150-1:200, all from Jackson ImmunoResearch Laboratories, Inc.). The slides were exposed to Hoechst stain (1:2,000; Invitrogen) for 1 min. For microscopic analysis, a fluorescence microscope (E800; Nikon) was used. The fluorescence microscope was equipped with a digital camera (DXM 1200F; Nikon) and with either a 20×NA 0.50 or 40×NA 0.75 objective lens (Plan Fluor; Nikon). Recordings were made on postfixed tissues at 24° C. using NIS-Elements, F3 (Nikon) acquisition software. Images were cropped, merged, and optimized using Photoshop 9.0 (Adobe) by making minor adjustments to contrast, and were arranged using Canvas X (Deneba Software).

Isolation of the Retina and Flow Cytometric Analysis. Following intracardiac perfusion with PBS, retinas were removed by dissection and processed to single-cell suspension as previously described (Kerr, E. C., B. J. Raveney, D. A. Copland, A. D. Dick, and L. B. Nicholson. 2008. Analysis of retinal cellular infiltrate in experimental autoimmune uveoretinitis reveals multiple regulatory cell populations. J Autoimmun 31:354-361, Luger, D., P. B. Silver, J. Tang, D. Cua, Z. Chen, Y. Iwakura, E. P. Bowman, N. M. Sgambellone, C. C. Chan, and R. R. Caspi. 2008. Either a Th17 or a Th1 effector response can drive autoimmunity: conditions of disease induction affect dominant effector category. J Exp Med 205:799-810). The following fluorochrome-labeled mAbs were purchased from BD, BioLegend, eBioscience or AbDSerotec, and used according to the manufacturers' protocols: PE-conjugated anti-CD11b, CD206 (MMR), and IL-4Rα antibodies; PerCP-cy5.5-conjugated anti-Ly6C and CD11b antibodies; allophycocyanin (APC)-conjugated anti-CD115, TCRβ, FoxP3 and CD204 antibodies, Alexa 647-conjugated anti-Dectin-1 antibody; and Pacific Blue/Brilliant Violet-conjugated anti-TCRβ, CD4 and CD45.2 antibodies. FoxP3 staining was performed using the Foxp3 staining buffer set (eBioscience), according to the manufacturer's protocol. Cells were analyzed on a FACS LSRII cytometer using FACSDiva software (both from BD). Analysis was performed with FlowJo software (Tree Star, Inc.). In each experiment, relevant negative and positive control groups were used to determine the populations of interest and to exclude the rest.

In Vivo Fluorescence Imaging. Mice are anesthetized and gently immobilized using a plastic apparatus. For visualization of the retina, a drop of 0.5% Tropicamide (Dr. Fischer) is used to dilate the pupil and a drop of ophthalmic lubricant (Celluspan; Dr. Fischer) is used to allow placement of a glass coverslip on the eye. Mice were injected with Dextran Rhodamine (1 mg per animal; Sigma-Aldrich) i.v. for blood vessel visualization. Mice are placed under a Zoom Stereo Microscope SZX-RFL-2 (Olympus) equipped with a fluorescence illuminator and a Pixelfly QE charge-coupled device camera (PCO). The excitation and emission for the red filter set are 510-550 nm and 590 nm (long pass), respectively. The green filter set is 460-490 nm for excitation and 510-550 nm for emission. Fluorescence exposure time is 50 ms. Images are acquired using the Camware camera-controlling software program (PCO). Image analysis is performed using ImageJ 1.43 software (W. Rasband, National Institutes of Health, Bethesda, Md.).

Statistical Analysis. Data are analyzed using a Student's t test to compare between two groups. One-way ANOVA is used to compare several groups. Fisher's LSD procedure is used for follow up pairwise comparison of groups after the null hypothesis had been rejected (F<0.05). Results are presented as mean±SE. In the graphs, y-axis error bars represent SE. For the uveitis study, Levene's test was used to check equality of variance. In the case of equal variances, data were analyzed using a Student's t test to compare between two groups, or by one-way ANOVA to compare several groups. Tukey's HSD test was used for follow-up pairwise comparison of groups after the null hypothesis was rejected (p<0.05). In the case of unequal variances, data were log-transformed to achieve equal variances when possible; otherwise, the Kruskal-Wallis test was used to compare several groups, followed by Dunn's test. Results are presented as mean±SE. In the graphs, y-axis error bars represent SE.

Example 1

Isolation of Human Mononuclear Cells that Express High Level of $CX_3CR1$ and Low Level of CCR2 from PBMC In humans, three populations of monocytes are defined by the expression of CD14 and CD16, namely: $CD14^+CD16^-$, $CD14^+CD16^+$, and $CD14^{dim}CD16^+$. The $CD14^+CD16^-$ monocytes represent 80% to 90% of blood monocytes, and express high levels of the chemokine receptor CCR2 and low levels of the chemokine receptor $CX_3CR1$ (the receptor of Fractalkine). In contrast to this major subset, human CD16+ monocytes express high levels of $CX_3CR1$ and low levels of CCR2 (Cros et al., 2010). According to Cros et al (2010), gene expression analyses indicated similarities between human $CD14^{dim}CD16^+$ and murine patrolling $Gr1^{dim}$ monocytes. The $CD14^{dim}CD16^+$ cells are bona fide monocytes involved in the innate local surveillance of tissues and the pathogenesis of autoimmune diseases.

In order to isolate from PBMC the $CD14^{dim}CD16^+$ cells that express high level of $CX_3CR1$ and low level of CCR2, we used the combined method of negative selection of CCR2 ($CCR2^+$ depletion) and positive selection of $CD14^+$ ($CD14^+$) while isolation of $CD14^+$ from PBMC was used as control, as illustrated in Scheme I.

SCHEME I

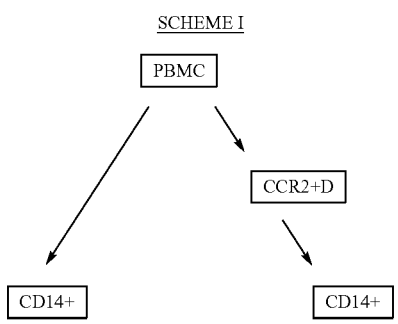

Enriching CD14dimCD16+Cell Population:

(i) Isolation of mononuclear cells from human peripheral blood: Fresh blood (8 ml) collected from healthy donor was diluted 1:1 with 2.5% FCS in PBS, and loaded on a Ficoll gradient (Ficoll-Paque plus, Amersham Biosciences). Tubes were centrifuged for 20 min at 1000 g, at 20° C. The mononuclear cell phase was collected and washed twice with PBS.

(ii) CCR2+ depletion: First the mononuclear cells were Fc-receptor-blocked by treatment with FcR blocking reagent (2.5 µl/$10^6$ cells) (130-059-901, MiltenyiBiotec) for 15 minutes at room temperature. Then, without washing, the monoclonal anti-human CCR2-biotin reagent (FAB151B, R&D Systems) was added (10 µl/$10^6$ cells) and incubated for 35 minutes at 2°-8° C. Then the cells were washed with cold MACS™ buffer (1 mM EDTA, 2% FCS in PBS) and streptavidin microbeads (130-048-101, MiltenyiBiotec) were added (20 µl/$10^7$ cells) for 20 minutes at 2°-8° C. The cells were washed and resuspended with 0.5 ml of MACS™ buffer. The depletion of the CCR2+ cells was done with LD column (130-042-901, MiltenyiBiotec) according to the manufacturers' protocols.

(iii) Isolation of CD14+ cells: The cells were resuspended with MACS™ buffer (80 µl/$10^7$ cells) and CD14+ microbeads (130-050-201, MiltenyiBiotec) were added (20 µl/$10^7$ cells) for 15 minutes at 2°-8° C. Then, the cells were washed and resuspended with 0.5 ml of MACS buffer. The positive selection of the CD14+ cells was done by using magnetic separation on LS column (130-042-401, MiltenyiBiotec) according to the manufacturer's protocols.

(iv) Fluorescence-activated cell sorting (FACS™) staining of human mononuclear cells All samples were stained according to the manufacturers' protocols. All samples were filtered through 70 µm nylon mesh and blocked with FCR blocking reagent (30 µl/$10^6$ cells) (130-059-901, MiltenyiBiotec) for 15 minutes at room temperature. The following fluorochrome-labeled anti-human monoclonal antibodies were used according to the manufacturers' protocols: PerCP conjugated anti CD45 (345809, BD), FITC conjugated anti CD115 (FAB329F, R&D Systems), Pacific Blue™ conjugated anti CD14 (BLG-325616), Alexa Fluor® 700 conjugated anti CD16 (BLG-302026), PE conjugated anti $CX_3CR1$ (MBL- D070-5) and PerCP conjugated anti CCR2 (BLG-335303).

Example 2

Inhibition of Neuronal Degeneration in the Retina

We choose to use several models of retinal degeneration: induction of EAU retinal intoxication with glutamate, a common mediator of toxicity under neurodegenerative conditions; optic nerve crush; elevated IOP model; and transgenic mice that best mimic the pathology of pigment epithelium degeneration.

EAU Induction. This is a model for human posterior uveitis. Since uveitis often results in the deterioration of the retina, it is considered a model of CNS neurodegeneration. Mice are injected subcutaneously with 500 µg peptide derived from human interphotoreceptor retinoid binding protein (IRBP), residues 1-20 (22) (AnaSpec, GL Biochem (Shanghai) Ltd., or the peptide synthesis unit at the Weizmann Institute), as a 1:1 emulsion with Complete Freund's Adjuvant (CFA) containing *Mycobacterium tuberculosis* strain H37.RA at a concentration of 2.5 mg/ml (1.25 mg/ml final). Mice are co-injected with 1 µg Bordella pertussis toxin (Sigma) intraperitoneally.

This regimen induces disease in 80-100% of animals by 14 days after immunization. The peak of disease occurs between d22 and d29 after immunization. Surviving RGCs are assessed 7 d after glutamate intoxication, or before, in the course of, and after the peak of the EUA disease, by immunostaining for Brn3a, a specific RGC marker (Nadal-Nicolás, F. M., M. Jimenéz-López, P. Sobrado-Calvo, L. Nieto-López, I. Cánovas-Martínez, M. Salinas-Navarro, M. Vidal-Sanz, and M. Agudo. 2009. Brn3a as a marker of retinal ganglion cells: qualitative and quantitative time course studies in naive and optic nerve-injured retinas. Invest. Ophthalmol. Vis. Sci. 50:3860-3868), and by retrograde labeling of RGCs with Fluoro-Gold, a commonly used method which labels the cell bodies of anatomically intact axons (Schori et al., 2002, supra; Schwartz and Kipnis, 2007, supra).

Intra-Vitreal Glutamate Toxicity Model. Elevation of glutamate has been reported in many CNS disorders. In its role as an excitotoxic compound, glutamate is one of the most common mediators of toxicity in acute and chronic (including optic nerve degeneration in glaucoma) degenerative disorders (Doble, 1999). This is therefore a general model for neurodegeneration of central nervous system nerves. When the glutamate is injected into the eye, this model is particularly representative of retinal ganglion neurodegeneration as it occurs in various diseases of the eye, such as retinal degeneration disorders, e.g. age-related macular degeneration or retinitis pigmentosa; anterior ischemic optic neuropathy, glaucoma or uveitis. Mice are anesthetized, treated with local anesthesia (Localin; Dr. Fischer) applied directly to the eye, and injected intravitreally with a total volume of 1 µl saline containing 400 nmol 1-glutamate (Sigma-Aldrich), as previously described (Yoles E, Friedmann I, Barouch R, Shani Y, Schwartz M. Self-Protective mechanism awakened by glutamate in retinal ganglion cells. J Neurotrauma. 2001, March; 18(3):339-4; Schori, H., E. Yoles, L. A. Wheeler, T. Raveh, A. Kimchi, and M. Schwartz. 2002. Immune-related mechanisms participating in resistance and susceptibility to glutamate toxicity. Eur. J. Neurosci. 16:557-564).

N-Methyl-N-Nitrosourea (MNU) Toxicity Model. A single systemic administration of MNU causes retinal degeneration in various animal species. The retinal degeneration is highly reproducible, and the photoreceptor cell loss occurs within seven days after MNU administration via apoptosis resembling human retinitis pigmentosa (Tsubura A, Yoshizawa K, Kuwata M, Uehara N. Animal models for retinitis pigmentosa induced by MNU; disease progression, mechanisms and therapeutic trials. Histol Histopathol. 2010 July; 25(7):933-44. Review)

Optic Nerve Crush in the Mice. A calibrated optic nerve crush induces progressive ganglion cell death due to retrograde signaling of axonal injury (Levkovitch-Verbin H, Harris-Cerruti C, Groner Y, Wheeler L A, Schwartz M, Yoles E. RGC death in mice after optic nerve crush injury: oxidative stress and neuroprotection. Invest Ophthalmol Vis Sci. 2000 December; 41(13):4169-74). In short, mice are anesthetized and subjected to severe crush injury in the intraorbital portion of the optic nerve, 1-2 mm from the eyeball. With the aid of a binocular operating microscope, the conjunctiva is incised and the optic nerve exposed. Using cross-action calibrated forceps and taking special care not to interfere with the blood supply, the nerve is crushed for 2 s.

Elevated TOP Model. Intraocular pressure (IOP) is a risk factor for glaucoma and since it may cause degeneration of the retina and optic nerve serves as a model for neurodegeneration in general and glaucoma in particular. Ischemic injury is produced as previously described (Da, T., and A. S. Verkman. 2004. Aquaporin-4 gene disruption in mice protects against impaired retinal function and cell death after ischemia. Invest. Ophthalmol. Vis. Sci. 45:4477-4483; Ben Simon, G. J., S. Bakalash, E. Aloni, and M. Rosner. 2006. A rat model for acute rise in intraocular pressure: immune modulation as a therapeutic strategy. Am. J. Ophthalmol. 141:1105-1111). In brief, after anesthesia, intraocular pressure (IOP) is elevated by introducing into the anterior chamber a micropipette, connected to a reservoir of isotonic salt solution (Saline). The reservoir is situated at an appropriate height, inducing pressure of 120 mm Hg for 60 min.

Transgenic Mice Models. Relevant transgenic mice are for example, choroideremia (CHM) knock-out mice (Tanya Tolmachova, Silene T. Wavre-Shapton, Alun R. Barnard, Robert E. MacLaren, Clare E. Futter, and Miguel C. Seabra. Retinal Pigment Epithelium Defects Accelerate Photoreceptor Degeneration in Cell Type-Specific Knockout Mouse Models of Choroideremia. Invest Ophthalmol Vis Sci. 2010 October; 51(10): 4913-4920.); and transgenic mice with a rhodopsin mutation (Pro23His) (Jane E. Olsson, Jon W. Gordon, Basil S. Pawlyk, Dorothy Roof, Annmarie Hayes, Robert S. Molday, Shizuo Mukai, Glenn S. Cowley, Eliot L. Berson, Thaddeus P. Dryja. Transgenic mice with a rhodopsin mutation (Pro23His): A mouse model of autosomal dominant retinitis pigmentosa. Neuron (1992) 9: 815-830).

Protocol. Monocytes for transplantation were isolated from the bone-marrow of syngeneic mice. PBMCs were labeled with microbeads conjugated to antibodies to CD3, CD19 and CD56 to deplete the T-cells, B-cells and NK cells. The unlabeled cells which passed through the magnetic column were collected. This fraction was labeled with anti-CD16 microbeads and loaded again on the magnetic column. The cells that passed through the column were collected and stained for analysis in the FACS with CD14 and CD16 fluorescent antibodies. In the PBMCs, 19% of total live cells are monocytes (CD14+). Out of the monocytes, about 10% are CD16+. In the final product about 90% of live cells are monocytes out of which CD16+ is less than 0.1%.

We then examine the ability of the above described sub-population to protect retinal ganglion cells following retinal damage when injected into the eye prior to or after the assault to the retinal ganglion cells.

Mice are treated by a single injection of autologous monocytes at different time points after damage onset. Two routes of administration are examined per each animal model: (i) Intra-vitreal injection and (ii) Sub-retinal injection. The endpoint of the study is evaluation of neuronal survival in the retina using morphological criteria and by counting the cellular element that survives in cress sections of the retina.

Subretinal injection of the monocyte sub-population is performed for example according to Warfinge et al., 2011; however any technique for injecting monocytes sub-retinally may be used. Animals are placed under general anesthesia, and vitreoretinal surgery is performed as previously described (K. Warfvinge, J. F. Kiilgaard, E. B. Lavik et al., "Retinal progenitor cell xenografts to the pig retina: morphologic integration and cytochemical differentiation," Archives of Ophthalmology, vol. 123, no. 10, pp. 1385-1393, 2005). Briefly, the pigs are pre-anesthetized with intramuscular injections consisting of midazolam, zolazepam, tiletamine, xylazine, ketamine, and methadone. They are then intubated, artificially ventilated, and anesthetized with isoflurane/oxygen. The operative pupil is dilated with topical phenylephrine, tropicamide, and atropine. The surgical field is prepared and draped in the usual sterile fashion before commencement of surgery. A localized 3-port pars plana vitrectomy is performed and green argon laser burns applied in a grid pattern to the area centralis of the retina. A retinotomy is prepared and the monocytes delivered via an appropriate needle to the subretinal space in the region corresponding to the laser burns. Correct graft placement is ascertained by direct visualization at the time of injection. Chloramphenicol is given prophylactically at the end of surgery to avoid infection.

Example 3

Treatment of Age-related Macular Degeneration with Monocyte Subpopulation

Albino rats are exposed to 12 hours of 3000-luxcyclic light for 1, 3, or 6 months. Fundus examination, fundus photography, fluorescein and indocyanine green angiography, and optical coherence tomography are performed prior to euthanization. Light-exposed animals are euthanized after 1, 3, or 6 months for histopathological evaluation. Retinas are examined for the presence of 4-hydroxy-2-nonenal- and nitrotyrosine-modified proteins by immunofluorescence staining (Daniel M. Albert et al., 2010. Development of choroidal neovascularization in rats with advanced intense cyclic light-induced retinal degeneration. Arch Ophthalmol. 2010; 128(2):212-222). The light-exposed animals are treated as described above by a single injection of autologous monocytes at different time points after damage onset. Two routes of administration are examined per each animal model: (i) Intra-vitreal injection and (ii) Sub-retinal injection. The endpoint of the study is evaluation of neuronal survival in the retina using morphological criteria and by counting the cellular element that survives in cress sections of the retina.

The Similarity Between AMD and Alzheimer's Disease. AMD and Alzheimer's disease are both chronic neurodegenerative disorders that affect a substantial proportion of elderly persons. Characteristic of these disorders is the irreversible loss of function, for which there is no cure. The degeneration occurring in AMD and Alzheimer's disease may, to some extent, have a common pathogenesis (Klaver et al., 1999. Is age-related maculopathy associated with Alzheimer's disease? The Rotterdam study. Am J Epidemiol; 150:963-8). Although the etiology of both AMD and Alzheimer's disease is largely unknown, the pathogeneses of the two diseases show some striking similarities. In AMD, early histopathological manifestations are extracellular drusen deposits and basal laminar deposits (Hageman, G S. & Mullins, R F. Molecular composition of drusen as related to substructural phenotype. Mol Vis 5, 28 (1999)). These lesions contain lipids, glycoproteins and glycosaminoglycans, which are presumably derived from a degenerating neuroretina. Accumulation of these deposits is associated with loss of photoreceptors and subsequent deterioration of macular function (Holz et al., Bilateral macular drusen in age-related macular degeneration. Prognosis and risk factors. Ophthalmology 101, 1522-8 (1994)). As noted above, an early pathologic hallmark in Alzheimer's disease is the presence of extracellular senile plaques (Selkoe, 1991. The molecular pathology of Alzheimer's disease. Neuron 6, 487-98). These plaques are composed of many components, including small peptides generated by proteolytic cleavage of a family of transmembrane polypeptides known as amyloid precursor proteins. Two peptides that are widely regarded as major contributors to the pathology of Alzheimer's disease are known as amyloid-β (Aβ) peptides. Shared components of amyloid deposits and drusen include proteins such as vitronectin, amyloid P, apolipoprotein E, and even the Aβ peptides and amyloid oligomers that are associated with amyloid plaques in Alzheimer's disease (Luibl et al., 2006. Drusen deposits associated with aging and age-related macular degeneration contain nonfibrillar amyloid oligomers. J Clin Invest 116, 378-85; Mullins et al., 2000. Drusen associated with aging and age-related macular degeneration contain proteins common to extracellular deposits associated with atherosclerosis, elastosis, amyloidosis, and dense deposit disease. Faseb J 14, 835-46; Yoshida et al., 2005. The potential role of amyloid beta in the pathogenesis of age-related macular degeneration. J Clin Invest 115, 2793-800).

The Aβ peptides present in Alzheimer's disease activate microglial cells to produce potentially neurotoxic substances such as reactive oxygen and nitrogen species, proinflammatory cytokines, complement proteins, and other inflammatory mediators that bring about neurodegenerative changes. The inflammatory response that has been associated with Alzheimer's disease often involves CD11b$^+$ activated microglia, representing the innate arm of the immune system in the CNS. CD11b$^+$ microglia were reported to be associated with age-related normal human brain (Streit, 2004. Microglia and Alzheimer's disease pathogenesis. J Neurosci Res 77, 1-8), and it is possible that such microglia are the ones that contribute both to age-related cognitive loss and to impaired neurogenesis (Monje et al., 2003 Inflammatory blockade restores adult hippocampal neurogenesis. Science 302, 1760-5). CD11b have also been found in patients with Alzheimer's disease (Akiyama & McGeer, 1990. Brain microglia constitutively express beta-2 integrins. J Neuroimmunol 30, 81-93). Moreover, inflammatory mediators are present in amyloid deposits as well as in drusen, suggesting a possible common role for the inflammatory pathway in AMD and Alzheimer's disease (Hageman et al., 2001. Molecular composition of drusen as related to substructural phenotype. Mol Vis 5, 28). A role for local inflammation in drusen biogenesis suggests that it is analogous to the process that occurs in Alzheimer's disease, where accumulation of extracellular plaques and deposits elicits a local chronic inflammatory response that exacerbates the effects of primary pathogenic stimuli (Akiyama et al., 2000. Inflammation and Alzheimer's disease. Neurobiol Aging 21, 383-421).

In view of the above, the efficacy of the monocyte subpopulation as defined above on AMD treatment, may be assessed using a model utilizing exposure of neurons to aggregated Aβ.

Example 4

Intravitreal Injection of Mouse Monocytes—Effect on Retinal Ganglion Survival after Glutamate Intoxication and Characterization of the Injected Cells Protocol:

Mice were anesthetized and intravitreally injected with 400 nmol L-glutamate (in 1 μl saline) into the right eye.— On the following day, cells were purified for intravitreal injection: CD115$^+$ Bone Marrow Monocytic Cells (BM-MCs) from mouse—bone marrow cells were harvested from the femurs and tibiae of donor mice (that carry a GFP reporter under the cx$_3$cr1 myeloid promoter), and enriched for mononuclear cells on a Ficoll density gradient. The CD115$^+$ BM monocyte population was isolated through Magnetic Activated Cell Sorting (MACS) system using biotinylated anti-CD115 antibodies and streptavidin-coupled magnetic beads (Miltenyi Biotec) for positive selection of the targeted population. Cells were injected intravitreally to the GT-intoxicated eye (through the same hole through which the GT was introduced the day before), 10$^5$ cells per mouse (in 1 μl PBS). A control group was injected with PBS.

On day 7 after injection of GT, mice were perfused and eyes were collected into 2.5% PFA overnight and then the solution was replaced to 1% PFA and the eyes were immersed for an additional 3-4 days, and further processed for immunohistological staining with the RGC marker, Brn3a. Four sections were quantified per sample, taken from different depths of the eye. Cells counted in the ganglion cell layer of the retina were Brn3a$^+$, IB-4$^-$ and Hoechst$^+$. The PBS-injected eyes served as negative control, and the non-injured, contralateral eyes from the same mice served as a positive control for RGC survival.

The injected mouse cells were traced in the eye by staining for GFP, and their phenotype was characterized by staining for several immune markers (cytokines, growth factors, phagocytosis markers).

Figure 1B:
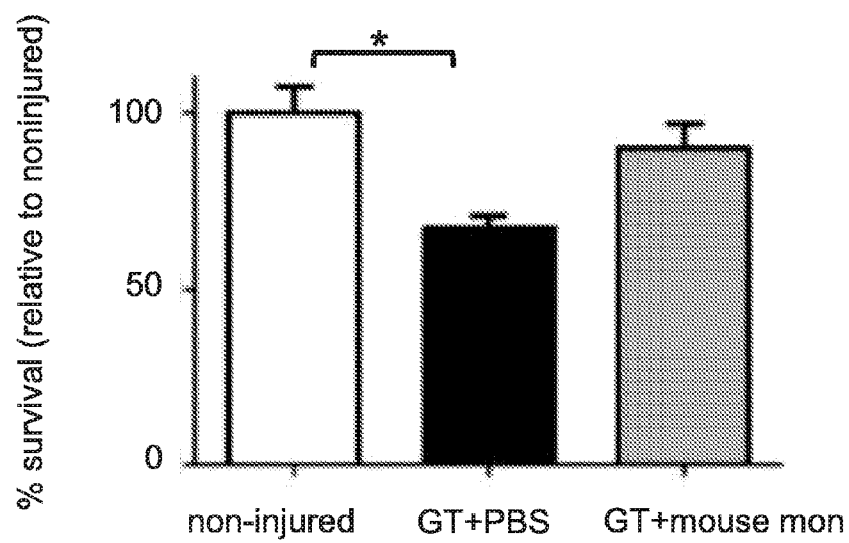
Figure 1C:
Figure 1D:
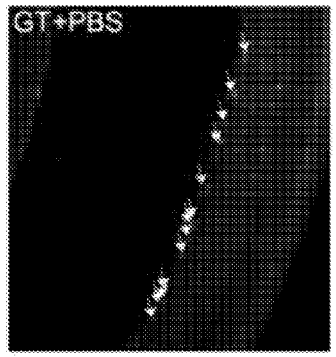
Figure 1E:
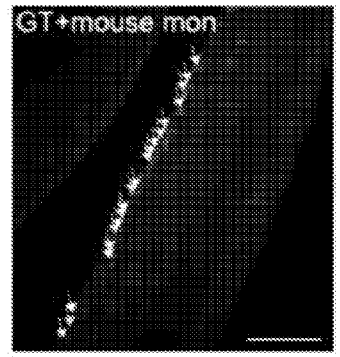
Figure 2A:
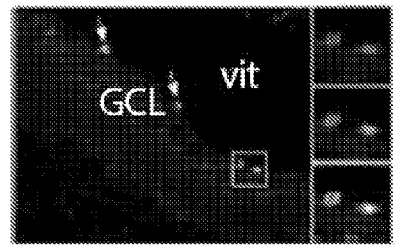
FIGS. 2A-H show micrographs depicting localization and characteristics of intravitreally-injected mouse monocytes. Representative micrographs of retinas from day 7 after glutamate intoxication, showing the expression of an array of cytokines and neurotrophic factors (red) by the injected mouse monocytes (CX3CR1-GFP, green). (A) TGFβ; (B) IL-10; (C) CD38; (D) IGF-1; (E) BDNF; (F) Arg-1 (Arginase-1); (G) TNF-α; (H) IL-1β. Non-specific staining of cells was done with Hoechst stain (blue). The injected cells were found in the vitreous and in proximity to injured RGCs, as well as in the subretinal space. Arrows point to double labeled cells; insets show higher magnification of representative cells (scale bar 50_m; inset scale 10_m). GCL—ganglion cell layer; SRS—subretinal space; vit—vitreous.
Figure 2A:
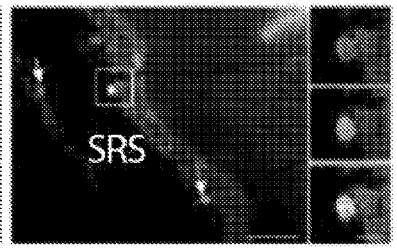
Figure 2B:
Figure 2B:
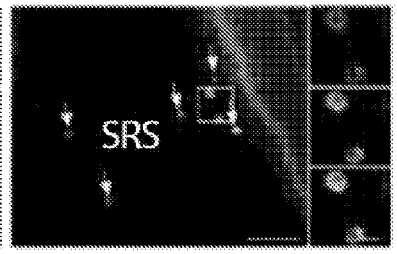
Figure 2C:
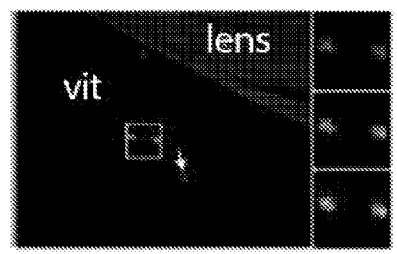
Figure 2C:
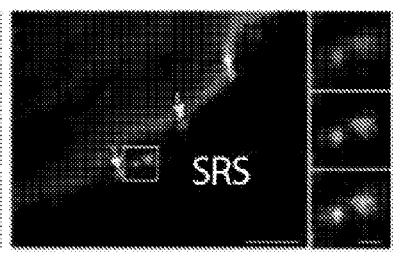
Figure 2D:
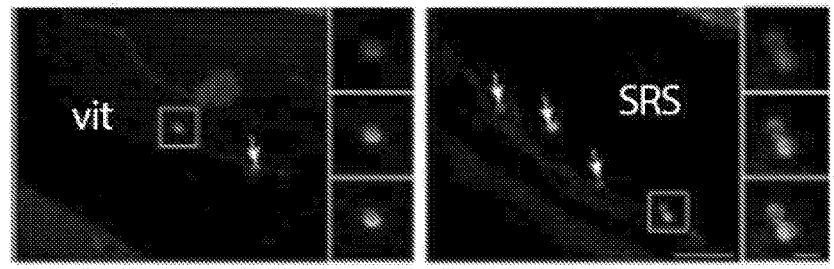
Figure 2E:
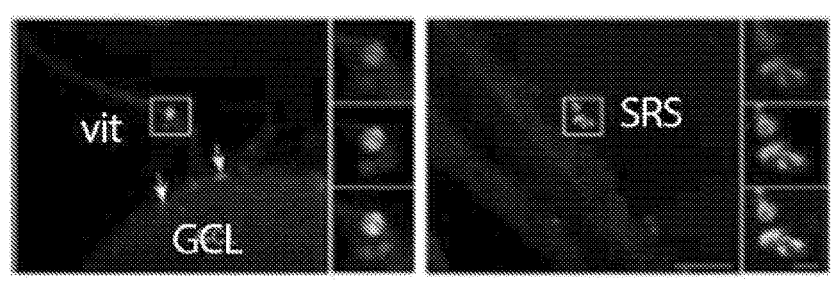
Figure 2F:
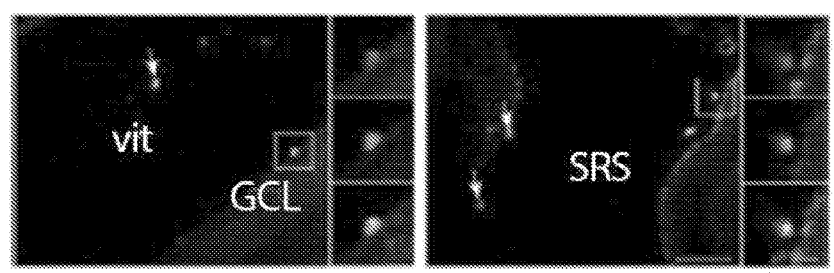
Figure 2G:
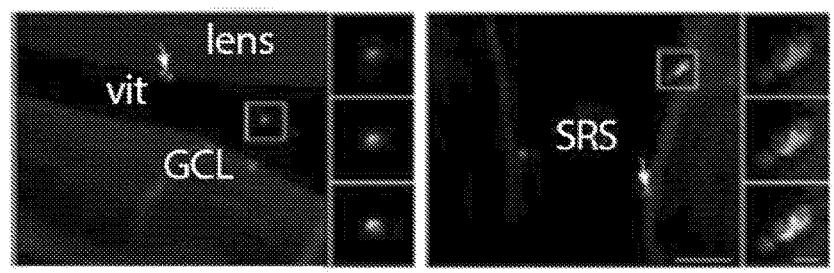
Figure 2H:
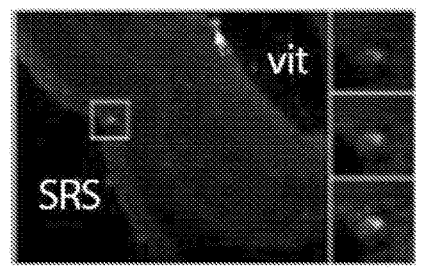

Results:

Mouse monocytes injected intravitreally had a protective effect on RGCs (FIGS. 1A-C). The monocytes were detected in the vitreous of the injected eyes, as well as in proximity to the ganglion cell layer (where damaged RGCs are located). In addition, some cells could be detected in the subretinal space (FIG. 2).

Double immunostaining for GFP together with an array of immune markers revealed the expression of IL-10, TGF-β, IGF-1, BDNF, CD36 and Arg-1 (Arginase-1), as well as TNFα and IL-1β, among the CX$_3$CR1-GFP$^+$ mouse monocytes (FIG. 2). Notably, this was a qualitative analysis, and so the frequency at which the different types of markers are expressed among the injected cells has yet to be determined.

Example 5

CNS-based Autoimmune Vaccination Augments the Infiltration of Macrophages and T Cells into the Retina after Optic Nerve Crush In order to show that the method to augment monocytes recruitment to the site of the damaged nervous system is immaterial, and that not only damage to the retina may be treated, but also damage to the optic nerve, endogenous cells were made to migrate to the site of damage of the optic nerve by immunization with a CNS-specific antigen.

Protocol:

[Cx3cr1$^{GFP/+}$→WT] BM chimeras were prepared by subjecting WT recipient mice to lethal whole-body irradiation (950 rad) while shielding the head, to prevent any direct insult to the retina or infiltration of myeloid cells other than that induced by optic nerve crush (ONC). On the subsequent day, mice were reconstituted with 5×10$^6$ bone marrow cells derived from Cx3cr1$^{GFP/+}$ transgenic mice by i.v. injection to the tail vein. In the resultant mice, only monocytes infiltrating from the blood carry the GFP label.

One group of mice was subcutaneously injected with a 100 μl emulsion containing 100 μg MOG altered peptide (45D; sequence: MEVGWYRSPFDRVVHLYRNGK) in 2.5 mg/ml complete Freund's adjuvant (Difco).

One week after the vaccination, mice (vaccinated and non-vaccinated) were anesthetized and subjected to severe crush of the right optic nerve under a binocular operating microscope, using cross-action forceps. The contralateral nerve was left undisturbed.

On d7 after ONC, mice were perfused and retinas were collected and processed to a single-cell suspension for flow cytometric analysis.

Figure 3A:
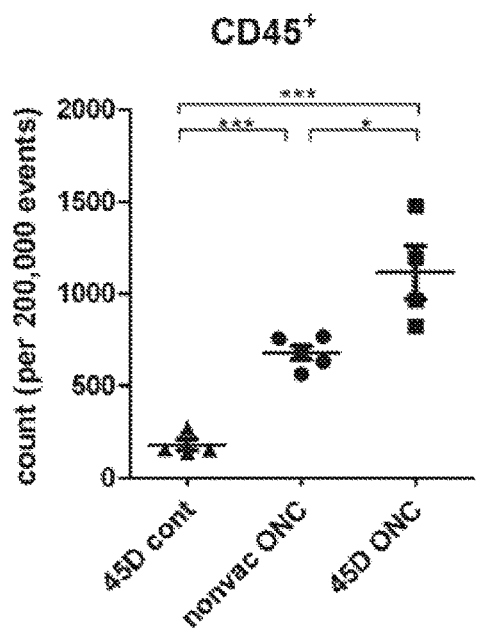
FIGS. 3A-C show that protective CNS-based autoimmune vaccination augments the immune response in the retina after optic nerve crush (ONC). Quantification of total leukocytes ($CD45^+$; A), infiltrating monocyte-derived macrophages ($CD11b^+GFP^+$; B) and T cells ($TCRβ^+$; C) in the retinas of chimeric mice 7 days after ONC. One group of mice was vaccinated with MOG-derived altered peptide (45D) 1 week prior to ONC. Contralateral retinas from the vaccinated group were used as noninjured controls. Graphs show mean±SE of each group. *, $P<0.05$; , $P<0.01$; *, $P<0.001$.

Results:

ONC resulted in an increase in total leukocytes in the retina (CD45$^+$), an increase which was enhanced in 45D-vaccinated injured mice (FIG. 3A).

Figure 3B:
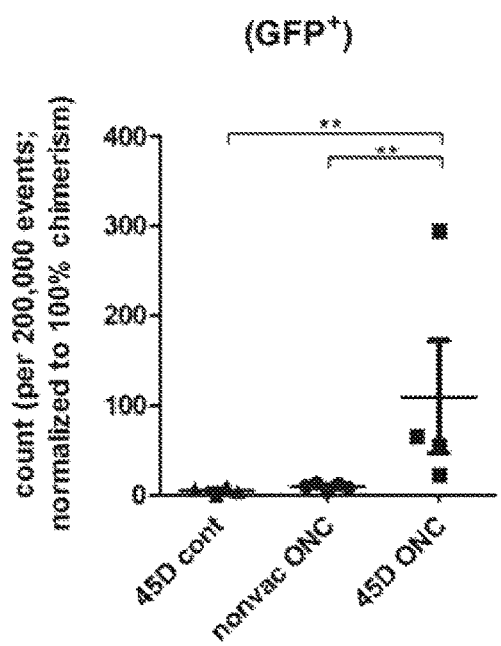
Figure 3C:
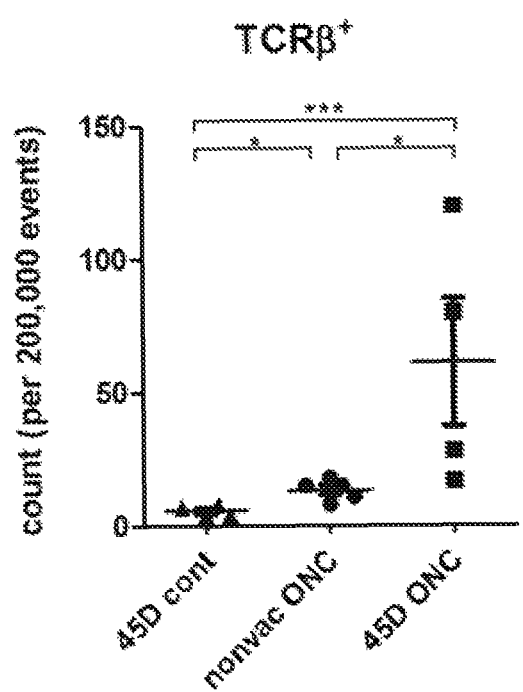

Macrophages and T cells were also increased in retinas of mice that had been vaccinated with 45D prior to ONC, compared to retinas from non-vaccinated, injured mice (FIGS. 3B and C).

Example 6

Assessment of the Capacity of CNS-based Autoimmune Vaccination to Confer Neuroprotection to Retinal Ganglion Cells after Optic Nerve Crush Protocol:

Correlation between the effect of vaccination on augmenting the number of peripheral monocytes in the damaged retina and survival of RGCs after optic nerve crush injury will be demonstrated in the following experiment. One group of mice is subcutaneously injected with a 100 μl emulsion containing 100 μg MOG altered peptide 45D (myelin oligodendrocyte glycoprotein (MOG)$_{35-55}$ altered at position 45 from serine to aspartic acid) in 2.5 mg/ml complete Freund's adjuvant (Difco).

One week after the vaccination, mice (vaccinated and non-vaccinated) are anesthetized and subjected to severe crush of the right optic nerve under a binocular operating microscope, using cross-action forceps. The contralateral nerve is left undisturbed.

On day 7 after ONC, mice are perfused and eyes are collected into fixative (2.5% PFA→1% PFA), and further processed for immunohistological staining with the RGC marker, Brn3a. Four sections are quantified per sample, taken from different depths of the eye. Cells counted in the ganglion cell layer of the retina are Brn3a$^+$, IB-4$^-$ and Hoechst$^+$. The noninjured, contralateral eyes from the non-vaccinated mice serve as a positive control for RGC survival (100%).

REFERENCES

Cros J, Cagnard N, Woollard K, Patey N, Zhang S Y, Senechal B, Puel A, Biswas S K, Moshous D, Picard C, Jais J P, D'Cruz D, Casanova J L, Trouillet C, Geissmann F (2010). Human CD14dim monocytes patrol and sense nucleic acids and viruses via TLR7 and TLR8 receptors. Immunity. 33(3):375-86

Doble (1999). The role of excitotoxicity in neurodegenerative disease: implications for therapy", PharmacolTher, 81:163-221.

Knoller N, Auerbach G, Fulga V, Zelig G, Attias J, Bakimer R, Marder J. B., Yoles E, Belkin M, Schwartz M, and Hadani M (2005) Clinical experience using incubated autologous macrophages as a treatment for complete spinal cord injury: Phase I study results J Neurosurg Spine 3:173-181.

London, A, Elena Itskovich, Inbal Benhar, Vyacheslav Kalchenko, Matthias Mack, Steffen Jung, and Michal Schwartz (2011). Neuroprotection and progenitor cell renewal in the injured adult murine retina requires healing monocyte-derived macrophages. The Journal of Experimental Medicine; 208(1):23-39.

Pitt et al. (2000). "Glutamate excitotoxicity in a model of multiple sclerosis", Nat Med, 6:67-70.

Shechter R, London A, Varol C, Raposo C, Cusimano M, Yovel G, Rolls A, Mack M, Pluchino S, Martino G, Jung S, Schwartz M (2009). Infiltrating blood-derived macrophages are vital cells playing an anti-inflammatory role in recovery from spinal cord injury in mice. PLoS Med 6(7): e1000113.

Tang J, Kern TS. Inflammation in diabetic retinopathy. Prog Retin Eye Res. 2011 September; 30(5):343-58. doi: 10.1016/j.preteyeres.2011.05.002. Epub 2011 May 25. Review Yoshida N, Ikeda Y, Notomi S, Ishikawa K, Murakami Y, Hisatomi T, Enaida H, Ishibashi T. Clinical evidence of sustained chronic inflammatory reaction in retinitis pigmentosa. Ophthalmology. 2013 January; 120(1): 100-5.

The invention claimed is:

1. A method for inhibition of neuronal degeneration, and/or protection of neurons from glutamate toxicity, or promotion of nerve regeneration in the retina or optic nerve, wherein the retina or optic nerve is damaged by a disease, disorder or condition of the eye, said method comprising administering to the eye of an individual in need thereof an effective amount of a monocyte subpopulation of peripheral blood mononuclear cells (PBMCs), said monocyte subpopulation of PBMCs having an amount of having a low relative amount, or substantially devoid, of CD3+ cells, CD19+ cells, CD56+ cells and CD16+ cells each not exceeding 5% of the total number of cells in the monocyte subpopulation.

2. The method according to claim 1, wherein the monocyte subpopulation of PBMCs has an amount of CD14$^+$ cells which exceeds 60% of the total number of cells in the monocyte subpopulation.

3. The method according to claim 1, wherein said disease, disorder or condition of the eye is a retinal degeneration disorder selected from the group consisting of age-related macular degeneration, retinitis pigmentosa, anterior ischemic optic neuropathy, glaucoma and uveitis.

4. The method according to claim 1, wherein said PBMCs are human PBMCs.

5. The method according to claim 1, wherein said PBMCs are autologous PBMCs.

6. The method according to claim 1, wherein said PBMCs are allogeneic PBMCs.

7. The method according to claim 1, wherein said PBMCs are formulated for injection.

8. The method according to claim 7, wherein said PBMCs are formulated for injection into the eye.

9. The method according to claim 8, wherein said PBMCs are injected into the vitreous body of the eye.

10. The method according to claim 8, wherein said PBMCs are injected into the sub-retinal space of the eye.

11. The method according to claim 1, wherein said PBMCs are activated by co-culturing with a piece of skin.

12. The method according to claim 1, wherein said PBMCs are not activated by co-culturing with a piece of skin.

13. The method according to claim 1, wherein said PBMCs are injected into the vitreous body of the eye.

14. The method according to claim 1, wherein said PBMCs are injected into the sub-retinal space of the eye.

15. A method for inhibition of neuronal degeneration, and/or protection of neurons from glutamate toxicity, in the retina or optic nerve, wherein the retina or optic nerve is damaged by a disease, disorder or condition of the eye, said method comprising administering to the eye of an individual in need thereof an effective amount of a monocyte subpopulation of peripheral blood mononuclear cells (PBMCs), said monocyte subpopulation of PBMCs having an amount of $CD14^+$ cells exceeding 60% of the total number of cells in the monocyte subpopulation and having an amount of $CD3^+$ cells, $CD19^+$ cells, $CD56^+$ cells and $CD16^+$ cells each not exceeding 5% of the total number of cells in the monocyte subpopulation.

16. The method according to claim 15, wherein said disease, disorder or condition of the eye is a retinal degeneration disorder selected from the group consisting of age-related macular degeneration, retinitis pigmentosa, anterior ischemic optic neuropathy, glaucoma and uveitis.

17. The method according to claim 15, wherein said PBMCs are human PBMCs.

18. The method according to claim 15, wherein said PBMCs are autologous PBMCs or allogeneic PBMCs.

19. The method according to claim 15, wherein said PBMCs are formulated for injection into the eye.

20. The method according to claim 15, wherein said PBMCs are injected into the vitreous body or the sub-retinal space of the eye.

* * * * *